US007127287B2

(12) United States Patent
Duncan et al.

(10) Patent No.: US 7,127,287 B2
(45) Date of Patent: Oct. 24, 2006

(54) DISTRIBUTED FUNCTIONAL ELECTRICAL STIMULATION SYSTEM

(75) Inventors: Michael Duncan, Lane Cove (AU); Ian Bruinsma, Lane Cove (AU); Zoran Milijasevic, Lane Cove (AU); Andrew Barriskill, Lane Cove (AU)

(73) Assignee: Neopraxis Pty Limited, Lane Cove (AU)

( * ) Notice: Subject to any disclaimer, the term of this patent is extended or adjusted under 35 U.S.C. 154(b) by 544 days.

(21) Appl. No.: 10/360,651

(22) Filed: Feb. 10, 2003

(65) Prior Publication Data

US 2003/0171785 A1  Sep. 11, 2003

(30) Foreign Application Priority Data

Feb. 11, 2002  (AU)  ............................ PS0428

(51) Int. Cl.
*A61N 1/00* (2006.01)
*A61N 1/08* (2006.01)
(52) U.S. Cl. .............................. 607/2; 607/39; 607/40; 607/49; 607/60; 607/148
(58) Field of Classification Search ................ 607/117, 607/148, 2, 60, 61; 307/112, 113
See application file for complete search history.

(56) References Cited

U.S. PATENT DOCUMENTS

| | | | |
|---|---|---|---|
| 3,585,707 A | 6/1971 | Stevens | |
| 4,428,377 A | 1/1984 | Zollner et al. | |
| 4,459,989 A | 7/1984 | Borkan | |
| 4,528,984 A | 7/1985 | Morawetz et al. | |
| 4,628,934 A * | 12/1986 | Pohndorf et al. | ............. 607/27 |
| 4,835,853 A | 6/1989 | Hirschberg | |
| 4,934,368 A | 6/1990 | Lynch | |
| 5,038,781 A | 8/1991 | Lynch | |
| 5,081,989 A | 1/1992 | Graupe et al. | |
| 5,167,229 A | 12/1992 | Peckham et al. | |
| 5,522,865 A | 6/1996 | Schulman et al. | |
| 5,562,715 A | 10/1996 | Czura et al. | |

(Continued)

FOREIGN PATENT DOCUMENTS

DE    196 32 705 A1   2/1998

(Continued)

OTHER PUBLICATIONS

PCT/AU2003/000043 International Search Report, Jun. 19, 2003.

*Primary Examiner*—Mark Bockelman
(74) *Attorney, Agent, or Firm*—Jagtiani + Guttag

(57) ABSTRACT

A multi-purpose, functional electrical stimulation (FES) system 10 includes an implantable stimulator unit 12 for stimulating a plurality of different sites in a patient's body 14. A transmitter 20 is arranged externally of the patient's body 14 for supplying signals transcutaneously to the stimulator unit 12. A controller 16 is in communication with the transmitter 20. At least one implantable switching node 26 has an input terminal 30 in electrical communication with the stimulator unit 12 and a plurality of output terminals to each of which one of a further switching node 26 and a stimulating element 24 is connected. The switching node 26 including addressing circuitry 44 for switching at least one output terminal into electrical connection with the input terminal 30 of the switching node 26 in response to a control signal received from the controller 16 via the stimulator unit 12.

15 Claims, 4 Drawing Sheets

| U.S. PATENT DOCUMENTS | | | | FOREIGN PATENT DOCUMENTS | | |
|---|---|---|---|---|---|---|
| 5,776,171 | A | 7/1998 | Peckham et al. | EP | 0 165 049 A2 | 12/1985 |
| 5,895,414 | A | 4/1999 | Sanchez-Zambrano | GB | 2092004 | 8/1982 |
| 6,163,725 | A | 12/2000 | Peckham et al. | WO | WO 83/04182 | 12/1983 |
| 6,213,995 | B1 | 4/2001 | Steen et al. | WO | WO 95/10323 | 4/1995 |
| 6,272,382 | B1 | 8/2001 | Faltys et al. | | | |
| 2001/0000187 | A1 | 4/2001 | Peckham et al. | | | |

\* cited by examiner

DISTRIBUTED FUNCTIONAL ELECTRICAL STIMULATION SYSTEM

FIELD OF THE INVENTION

This invention relates to a multi-purpose, functional electrical stimulation (FES) system. More particularly, the invention relates to a distributed, multi-purpose, FES system and to a switching node for use in such a system.

BACKGROUND TO THE INVENTION

Neurological impairment, such as spinal cord injury (SCI), can occur in people of any age, and is often caused by injuries sustained in accidents associated with motor vehicles, firearms, sports injuries, and the like. Many of the individuals who sustain such injuries are young male adults between the ages of 16 and 30 who, up to the point of the accident, have lead active and healthy lives.

In the USA, the prevalence of neurological impairment resulting from SCI is estimated at between 712 and 906 per million with the incidence of SCI being calculated at between about 30 and 40 per million. It is widely recognised that SCI has a large impact on society in general and is a sudden and irreversible change to an individual's quality of life.

In order to define SCI, it should be understood that an SCI is a traumatic lesion to the spinal cord and the associated nerves. Thirty-one spinal nerves originate from the spinal cord and can be grouped as follows: 8 cervical (C1 to C8), 12 thoracic.(T1 to T12), 5 lumbar (L1 to L5), 5 sacral (S1 to S5) and 1 coccygeal. An injury to the spinal cord can result in varying degrees of impairment depending on where and to what extent the spinal cord is injured. In general, the higher up on the spinal cord the injury, the more severe the resulting impairment.

People suffering from an SCI are essentially categorised into two main groups: tetraplegics and paraplegics.

Tetraplegics are individuals who have sustained an injury to one of the eight cervical segments of the spinal cord, C1 to C8. Such an injury results in impaired use of the arms and hands as well as the legs. A person who has suffered such an injury generally experiences significant loss of sensation and volitional body movement as well as the loss of volitional bladder and bowel control. Many tetraplegics may also have loss of psychogenic and impaired reflex erections.

Paraplegics are individuals who have sustained an injury at the thoracic level, T1 to T12. These individuals usually have sensation and volitional control over their upper limbs, but have lost sensation and control of their lower limbs and bladder and bowel control, as well as erection problems in males.

Due to SCI individuals being unable to control bladder function, individuals must regularly self cathertise. This procedure is problematic, especially for females, and can result in an increase in the incidence of urinary tract infections. Still further, persons suffering from SCI must often undertake lengthy bowel evacuation procedures using, for instance, digital evacuation. SCI patients are also prone to secondary medical problems, such as pressure sores, osteoporosis, muscular atrophy in the lower limbs, muscle spasticity, deep vein thrombosis, cardiovascular disease and depression. Pressure sores are caused by the occlusion of blood flow during sitting and lying. They are a major health problem which may require surgery to repair and months of rehabilitation including requiring the patient to remain lying on their abdomen for an extended period of time.

Therefore, whilst restoration of bladder and bowel control is a primary need of SCI individuals, reduced incidence of pressure sores is also highly needed. This, together with the ability to exercise and stand and step, are functions that would greatly improve the quality of life of SCI individuals.

It is therefore evident that a large proportion of the population who have an SCI would benefit from a device that would be able to assist in the at least partial restoration of such lost functionality, in particular bowel and bladder function, erectile function, the reduction in the incidence of pressure sores and the provision of exercise and upright mobility. Various systems have been proposed by numerous organisations to deal with one or other of the functions that have been lost to SCI individuals.

The Applicant has previously developed a multi-purpose, functional electrical stimulation system. That system is described in International Patent Application PCT/AU03/00044, and is used to stimulate a number of sites in a patient's body using a single stimulator unit.

The stimulator unit is, in use, implanted in a costal region of the patient's body and may be required to stimulate regions such as the upper or lower extremities of the patient's body and the sacral and/or thoracic regions of the patient's spinal cord. Each site has multiple stimulation points which necessitates the leading of numerous electrical leads from the location of the stimulator unit to the relevant site.

In addition, it may occur that, at a later date, additional stimulation points at the site need to be stimulated which may necessitate the leading of additional electrical leads from the location of the stimulator unit to the stimulation point of the site.

SUMMARY OF THE INVENTION

According to a first aspect of the invention, there is provided a multi-purpose, functional electrical stimulation (FES) system which includes:

an implantable stimulator unit for stimulating a plurality of different sites in a patient's body;

a transmitter arranged externally of the patient's body for supplying signals transcutaneously to the stimulator unit;

a controller in communication with the transmitter; and at least one implantable switching node having an input terminal in electrical communication with the stimulator unit and a plurality of output terminals to each of which one of a further switching node and a stimulating element is connected, the switching node including an addressing means for switching at least one output terminal into electrical connection with the input terminal of the switching node in response to a control signal received from the controller via the stimulator unit.

Preferably, the stimulation system stimulates at least three sites in the patient's body. These sites may be a right upper or lower extremity of the patient's body, a left upper or lower extremity of the patient's body and a sacral/posterior region of a patient's spinal cord.

The system may have a switching node (referred to as a site switching node), or distributor, associated with each site. If desired, intermediate switching nodes may be arranged intermediate the stimulator unit and the site switching nodes.

This arrangement has the advantage that the number of electrical leads that needs to be implanted in a patient's body is substantially reduced. Rather than each stimulating element at each site requiring its own lead connected back to the implantable stimulator unit, a single lead may extend from the stimulator unit to each of one of the site switching nodes and the intermediate switching nodes. A multiplicity of leads may only extend from each site switching node, each lead terminating in at least one of the stimulating elements.

As indicated above, each output terminal of each switching node may communicate either with a stimulating element, in the form of an electrode, or with a further switching node.

The addressing means may include a switch element having the output terminals. The switch element, in turn, may include a switch member that connects a selected output terminal to the input terminal of the switching node.

The addressing means may include control logic for controlling operation of the switch element under control of the controller. The control logic may receive control commands via the control signal received from the controller via the stimulator unit.

The control signal may be a composite control signal and may include command or switching data relating to an output terminal to be selected and stimulation data for the stimulating element connected to the selected output terminal. Where an intermediate switching node is connected to the selected output terminal, the composite control signal may include switching data for the output terminal of each switching node which is to be selected.

One of the output terminals may be a non-stimulation terminal and, in a rest condition, ie where no control signal has been received by the switching node, the switch member may be connected to the non-stimulation output terminal.

A further output terminal may be a "status" terminal which, when the switch member is connected thereto enables the condition of the switching node to be determined. In other words, the switching node may operate in a self-diagnostic manner.

Each switching node may include a power supply means for supplying power to the addressing means, the power supply means being chargeable by a power component of the control signal. Thus, the power supply means may be a chargeable device which is charged by a power component of a control signal sent to the switching node. Instead, the power supply means may be a suitable power supply element which provides power to the switching node. The power supply element may be in the form of a battery. The battery may be a re-chargeable battery. The battery may be recharged via a charging device arranged transcutaneously relative to the patient's body, in use, or by an appropriate charging component of the control signal from the stimulator unit.

It is to be noted that, via appropriate signal telemetry from the controller, each stimulating element may serve as a sensing element for sensing activity at the site at which it is located. Thus, each switching node may be capable of bi-directional communication. The sensing function performed by each electrode may be, for example, the amount of a substance in the blood or tissue whereby an electrical signal is generated in response to the presence of such a substance. Instead, the sensing function may determine the absence or presence of a parameter or of a substance in response to applied stimulation. An example may be sensing the response of the surrounding nerves/muscles to applied stimulation to determine the efficacy of the applied stimulation, such as neural response measurements.

According to a second aspect of the invention, there is provided a switching node for use in a multi-purpose, functional electrical stimulation (FES) system, the switching node including:

an input terminal for receiving command signals from an implantable stimulator unit of the system;

a plurality of output terminals to each of which one of a further switching node and a stimulating element is connectable; and an addressing means for addressing the output terminals for connecting at least one of said output terminals to the input terminal upon receipt of an appropriate signal from the stimulator unit, in use, to enable an output signal to be output from that output terminal.

The addressing means may include a switch element having the output terminals. The switch element may include a switch member for connecting a selected output terminal to the input terminal.

The addressing means may include control logic for controlling operation of the switch element under control of the controller. The control logic may receive control commands via a control signal received from the controller via the stimulator unit.

The control signal may be a composite control signal and may include command or switching data relating to an output terminal to be selected and stimulation data for a stimulating element connected to the selected output terminal. Where an intermediate switching node is connected to the selected output terminal, the composite control signal may include switching data for the output terminal of each switching node which is to be selected.

One of the output terminals may be a non-stimulation terminal and, in a rest condition, ie where no control signal has been received by the switching node, the switch member may be connected to the non-stimulation output terminal.

A further output terminal may be a "status" terminal which, when the switch member is connected thereto enables the condition of the switching node to be determined. In other words, the switching node may operate in a self-diagnostic manner.

The switching node may include a power supply means for supplying power to the addressing means, the power supply means being chargeable by a power component of the control signal.

BRIEF DESCRIPTION OF THE DRAWINGS

The invention is now described by way of example with reference to the accompanying diagrammatic drawings in which:—

DETAILED DESCRIPTION OF THE DRAWINGS

Figure 1:
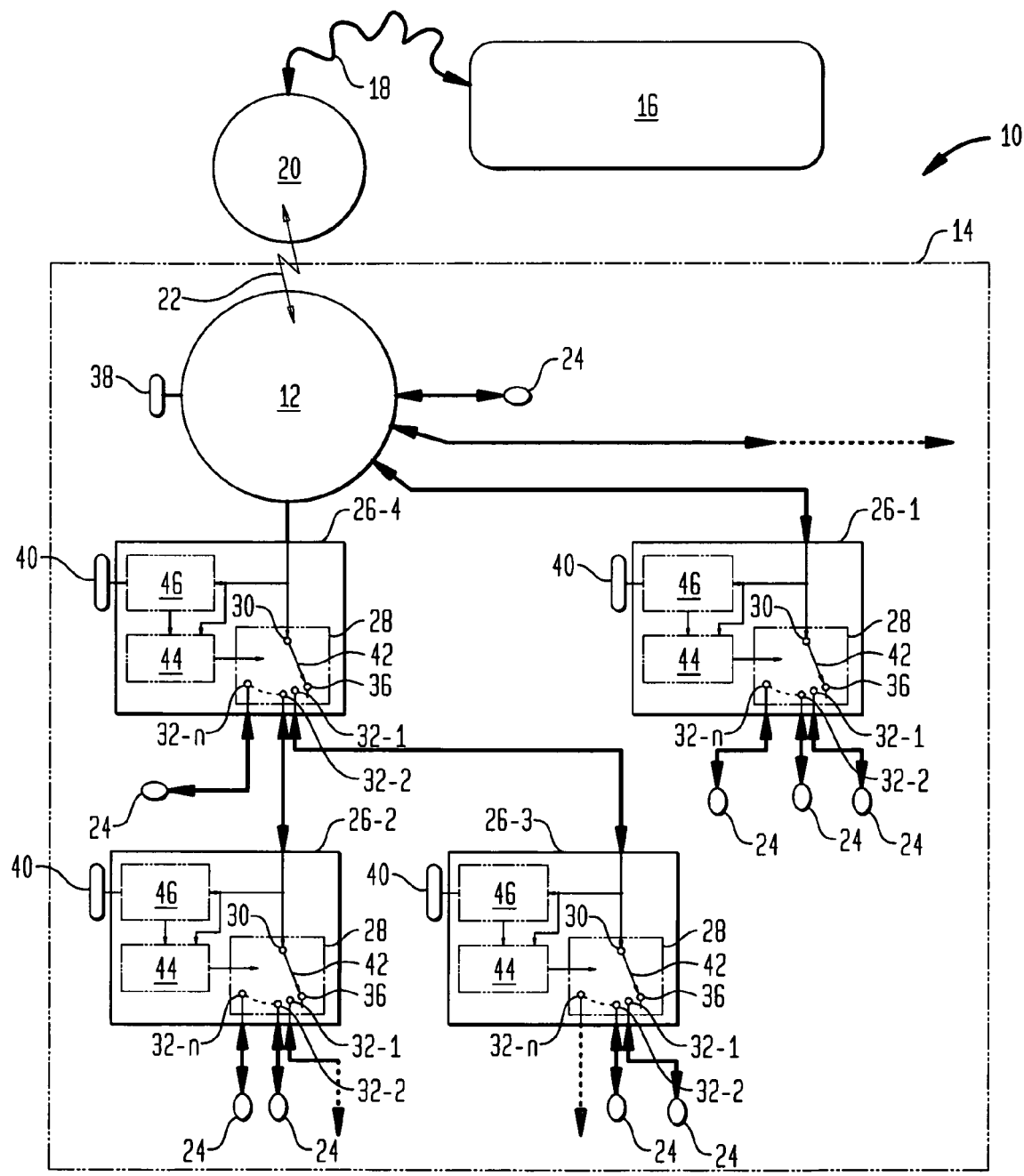
FIG. 1 shows a block diagram of a multi-purpose, functional electrical stimulation system, in accordance with a first aspect of the invention.

In the drawings, reference numeral 10 generally designates a multi-purpose, functional electrical stimulation (FES) system in accordance with a first aspect of the invention.

The system 10 includes an implantable stimulator unit 12 implanted, in use, in a patient's body represented schematically by the dotted lines 14. The stimulator unit 12 receives control signals from a controller 16 worn externally of the patient's body 14. The controller 16 sends control signals, in radio frequency (RF), over a connection cable 18 to an RF antenna 20 in the form of an RF transceiver coil. The coil 20 is, in use, placed in communication with the implanted stimulator unit 12 and communicates with the stimulator unit 12, in a bi-directional manner, transcutaneously, as represented by signal 22.

The operation of the components described above of the system 10 is described in greater detail in the applicant's co-pending PCT Application Nos. PCT/AU03/00043 and PCT/AU03/00044, the contents of which are incorporated in this specification by reference. Accordingly, the operation of the system 10 is not discussed in this specification in any greater detail.

The system 10, being a multi-purpose FES system, stimulates multiple sites in the patient's body 14. More particularly, at least a left lower extremity, a right lower extremity and a sacral and/or thoracic region of the spinal cord of the patient's body 14 are stimulated, in use. This assists a paraplegic/tetraplegic person in effecting a measure of control over those sites to facilitate standing/stepping and, in respect of the spinal cord regions which are stimulated, bladder control, bowel control and, in the case of males, to compensate for erectile dysfunction. It is also envisaged that the present invention could stimulate sites in the upper extremity of the body to provide a degree of upper body control.

The sites are stimulated by means of electrodes represented schematically at 24 in FIG. 1 of the drawings. Each site requires numerous electrodes 24 to effect stimulation at that site. To achieve this, each electrode 24 needs to receive a stimulation data signal from the stimulator unit 12 which, in turn, receives control signals from the controller 16 of the system 10. Thus, each electrode 24 needs to be in communication with the stimulator unit 12. Previously, this has been achieved by way of connecting each electrode 24 to the stimulator unit 12 using a dedicated electrical lead. It will be appreciated that, with such an arrangement, a large amount of leads need to be implanted in the patient's body which is not desirable due to the invasive nature of the implant surgery. By reducing the amount of leads required to be implanted, the invasiveness of the surgical procedure is reduced, together with the associated risk of infection and general size and "bulk" of the system implanted beneath the skin.

Accordingly, for each site in the patient's body, the system 10 includes a switching node or distributor 26. Each distributor 26 either communicates with the stimulator unit 12 directly as shown by distributor 26.1 or, instead, a distributor 26 at one of the sites may communicate with the stimulator unit 12 via an intermediate distributor 26. This is shown in the case of distributors 26.2 and 26.3 which communicate with the stimulator unit 12 via an intermediate distributor 26.4. Hence, in the examples shown in FIG. 1 of the drawings, the distributors 26.1, 26.2 and 26.3 are implanted proximate the sites to be stimulated in the patient's body 14 and are referred to as site distributors 26.1–26.3. The distributor 26.4 is an example of a distributor located remote from any of the sites to be stimulated and is an intermediate distributor. An intermediate distributor, however, also has the ability to deliver stimulation to a particular site.

Figure 5:
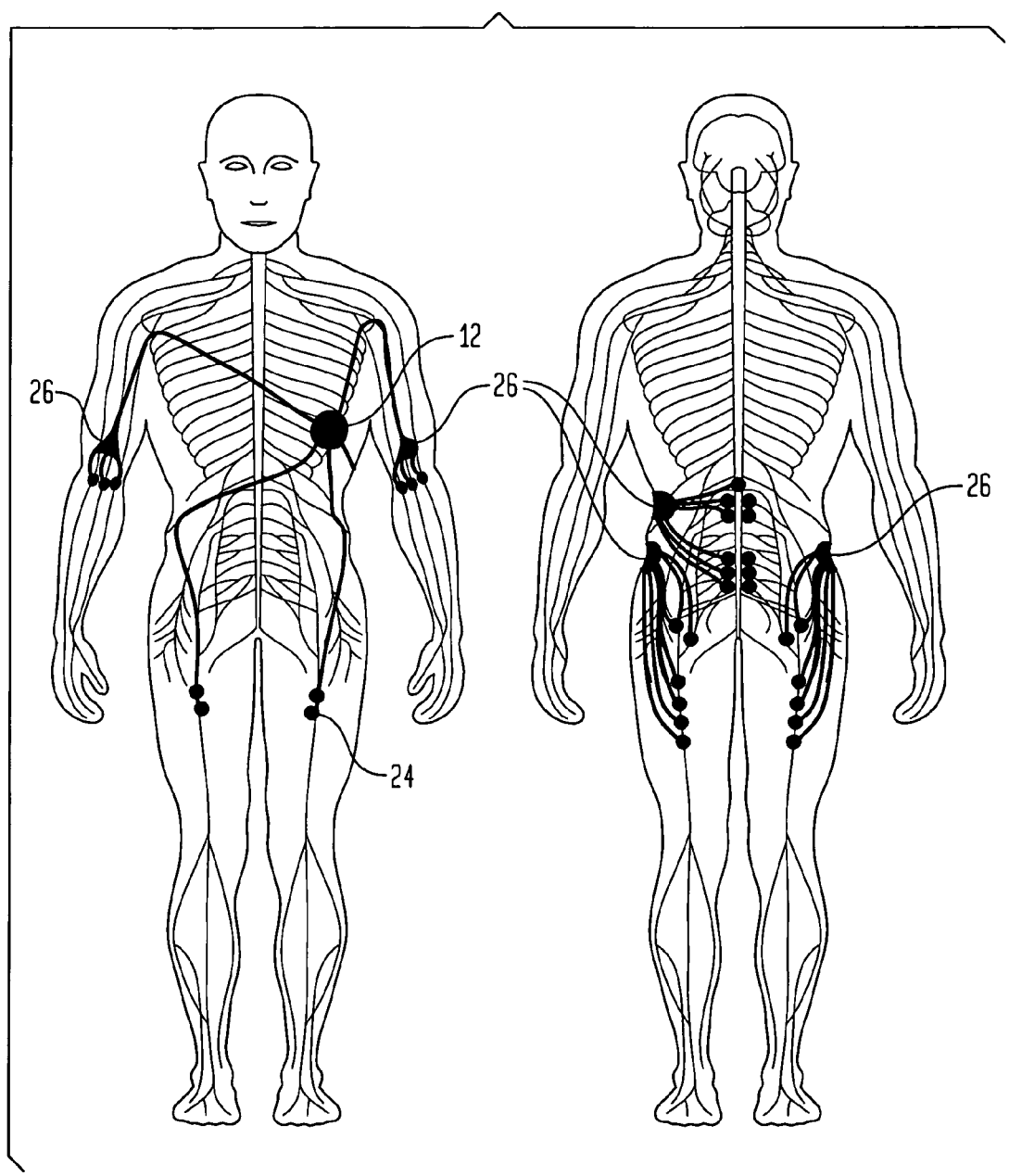
FIG. 5 shows a simplified view of one embodiment of the present invention following surgical implantation.

An example of a system of the present invention is shown diagrammatically in FIG. 5, which shows a plurality of distributors 26 located at specific sites within the body, and each connected by a single wire to the stimulator unit 12.

Each of the distributors 26 delivers stimulation to a plurality of regions via the relevant electrodes 24.

Figure 2:
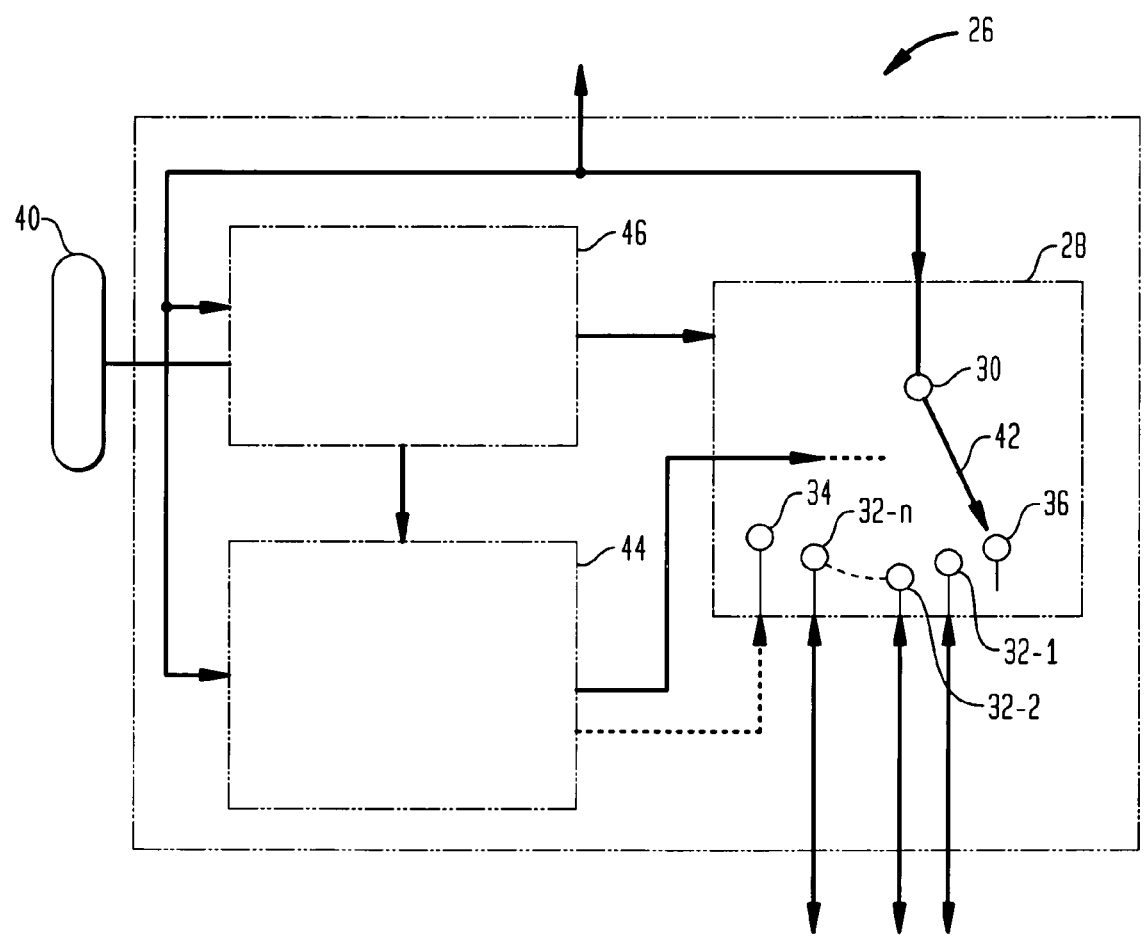
FIG. 2 shows a block diagram of a switching node, in accordance with a second aspect of the invention, for the system of FIG. 1.

Each distributor 26, a block diagram of which is shown in greater detail in FIG. 2 of the drawings, includes a switch element 28. The switch element 28 has an input terminal 30 and a plurality of output terminals or channels 32, 34 and 36.

It is to be noted that a closed circuit is formed by a return electrode 38 on the stimulator unit 12 and a return electrode 40 on each distributor 26. The return electrodes 38, 40 may be connected to each other by using the human body or by means of a return lead.

Referring again to FIG. 2 of the drawings, an electrode 24 or, where the distributor 26 is an intermediate distributor such as distributor 26.4, a further distributor 26 such as one of distributors 26.2 and 26.3 is connected to each channel 32 or selected channels 32.

In FIG. 1 of the drawings, the output terminal 34 of each distributor 24 is omitted, for the sake of clarity. Still further, it is to be noted, in the case of an intermediate distributor such as distributor 26.4, that either a distributor 26 or an electrode 24 can be connected to each of the channels 32 of the switch element 28.

The switch element 28 connects the appropriate channel 32–36 to the input terminal 30 via a switch member in the form of a wiper 42. The wiper 42 receives signals from and is controlled by control logic 44, as will be described in greater detail below.

Each distributor 26 also includes a power supply or power storage arrangement 46. The power storage arrangement 46 can be implemented in various ways. Firstly, the power storage arrangement 46 could be a storage device such as a capacitor which stores a charge from the input control signal from the stimulator unit 12. In that case, the power storage arrangement 46 is charged directly from the control signal output by the stimulator unit 12 and received from the controller 16. The storage device is charged to at least the amplitude of the stimulating signal and stores charge relative to the return electrode 40. Power is isolated from the return electrode 40 when stimulation is occurring, as appropriate.

Instead, the power storage arrangement 46 could be a battery. The battery is, preferably, a rechargeable battery. The battery is rechargeable either via the control signal received from the stimulator unit 12 or, instead, may be recharged via a unit (not shown) arranged externally of the patient's body 14 and which transmits an RF charging signal to the battery of each distributor 26 by being temporarily placed over the site of that distributor 26 to provide transcutaneous charging. In the case where the power storage arrangement is a battery, each of the distributors 26 could be linked via a wireless link. In such a configuration, the control signal is sent from the stimulator unit in the form of an RF signal which is detected by the desired distributor 26 so that controlled stimulation is delivered by the appropriate electrode 24.

Figure 3:
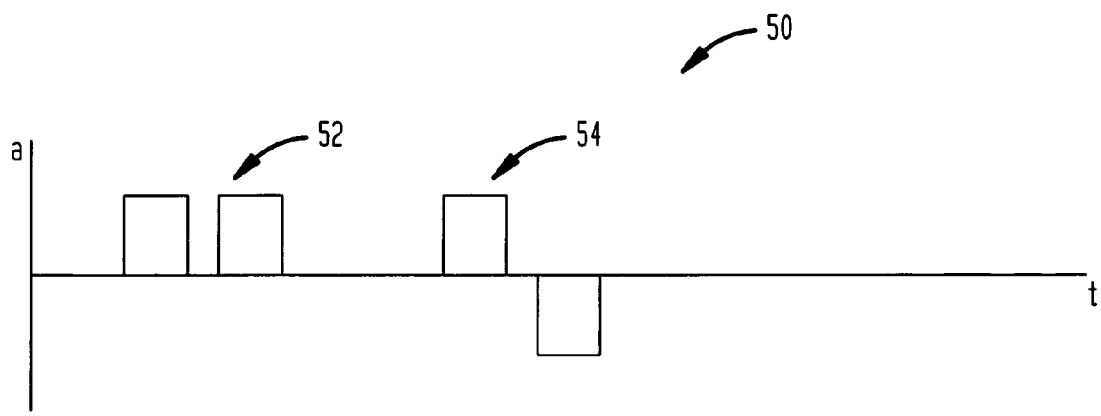
FIG. 3 shows a waveform of a control signal of the system.

Each control signal, a first version of which is shown at 50 in FIG. 3 of the drawings, is a composite control signal. The composite control signal 50 includes a command component 52 and a stimulation data component 54.

The command component 52 of the signal 50 determines which channel 32 is to be selected by the switch element 28 of the addressed distributor 26. Accordingly, the switch element 28 is, in effect, a controllable switching unit controlled by the control logic 44. Once the control logic 44 has determined which channel 32 is to be activated, the appropriate signal is sent from the control logic 44 to the wiper 42 of the switch element 28 to switch the wiper 42 from the terminal 36 to the appropriate channel 32. After this has occurred, the stimulation data component 54 is output on the appropriate channel 32 to the appropriate electrode 24.

Figure 4:
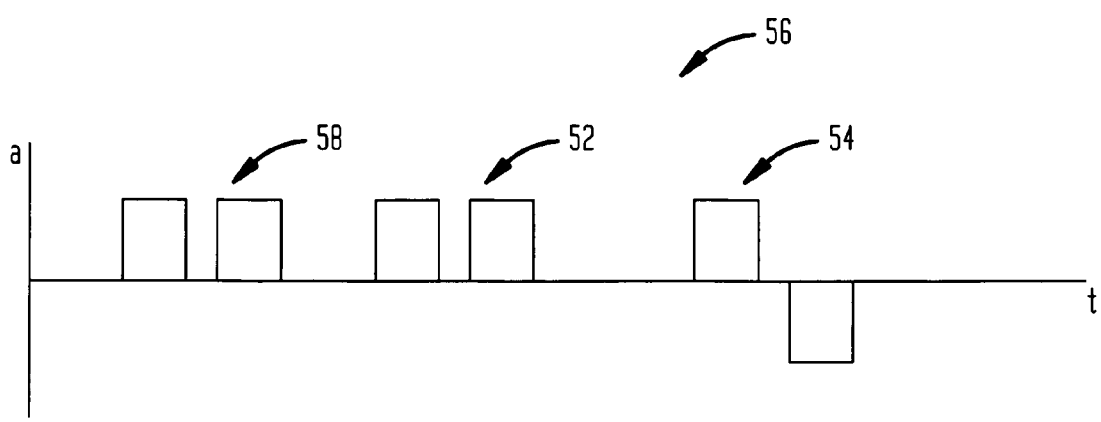
FIG. 4 shows a waveform of another control signal of the system.

Referring to FIG. 4 of the drawings, a second embodiment of a composite control signal 56 is illustrated. With reference to FIG. 3 of the drawings, like reference numerals refer to like parts unless otherwise specified. In this case, the control signal 56 is intended for an intermediate distributor such as distributor 26.4 and includes a first command component 58, a second command component 52 and a stimulation data component 54. The first command component 58 determines which channel 32 of the intermediate distributor 26.4 is to be opened by connecting that channel 32 to the input terminal 30 of the distributor 26.4. As shown in FIG. 1 of the drawings, the site distributor 26.3 is connected to channel 32.1 of the distributor 26.4 while the site distributor 26.2 is connected to channel 32.2 of the intermediate distributor 26.4.

Accordingly, when a composite signal 56 is received by the distributor 26.4, the power storage component 46 extracts the charging component from the command signal 58 and the data component (being the parts 52 and 54) of the command signal 56 is conveyed to the control logic 44 of the distributor 26.4. The control logic 44 determines from the command component 58 of the signal 56, which channel 32 is to be opened and connects the wiper 42 to that channel. For example, assuming the distributor 26.2 is associated with the right extremity of the patient's body 14 and that site is to be stimulated, the control logic 44 connects channel 32.2 to the input terminal 30 of the switch element 28. Once this connection has been made, the data component of the composite signal 56 is fed through to the distributor 26.2.

In the distributor 26.2, the command component 52 is used to power the power storage component 46 and the stimulation data component 54 and the command component 52 is fed to the control logic 44 of the distributor 26.2. The control logic 44 determines, from the command component 52 of the signal 56, which channel 32 of the distributor 26.2 is to be opened and connects that channel to the input terminal 30 of the switch element 28 of the distributor 26.2. The stimulation data component 54 of the signal 56 is then output on the relevant channel 32 to the electrode 24 connected to that channel 32 to effect stimulation at the site.

Each distributor 26 has a fail-to-safe setting in the sense that, in the absence of power to the distributor 26, the control logic 44 operates to switch the wiper 42 to the channel or terminal 36 which is a "no-connection" terminal.

By appropriate selection from the controller 16, each electrode 24 also serves as a sensing device for sensing physiological, anatomical and electrical activity at the site at which the electrode is located. Accordingly, each distributor 26 is capable of bi-directional communication with the stimulator unit 12 and, accordingly, with the controller 16. When the electrodes 24 operate in a sensing manner, the control logic 44 is operable to delay the switching of the wiper 42 to the "No-connection" terminal 36 in order to allow data to be transmitted to the stimulator unit 12 after receipt of the stimulation data component 54 of the signal 50, 56 by that electrode 24. In the case where no data are to be fed back to the stimulator unit 12, the wiper 42 may switch to the output terminal 36 on, or soon after, the positive going, second part of the bi-phasic pulse 54 illustrated in FIGS. 3 and 4. Conversely, when sensing data are to be transmitted to the stimulator unit 12, the switching of the wiper 42 to the terminal 36 is delayed for a predetermined period of time after the end of the stimulation data component 54.

The system 10 is, to a large extent, self-diagnostic as are the various components thereof. Accordingly, by an appropriate command from the controller 16, the control logic 44 of each distributor 26 operates to switch to the channel or terminal 34 (FIG. 2). When in this mode, the status of that distributor 26 can be determined by interrogation by the control logic 44 and appropriate data fed back via the stimulator unit 12 to the controller 16.

Finally, it is also to be noted in FIG. 1 of the drawings that the stimulator unit 12 can include electrodes 24 connected directly to the stimulator unit 12 rather than via a distributor 24.

Hence, it is an advantage of the invention that a system 10 and distributor 26 are provided which considerably reduce the number of electrical leads required to be implanted for a multi-purpose, FES system. This reduces the invasiveness of the implantation procedure, the likelihood of rejection of the system by the patient's body and the likelihood of infection occurring in the patient's body as a result of the implantation process.

In addition, the applicant believes that such a system will be more comfortable for the patient.

It is conceivable that, after the system 10 has been implanted, additional points at a site of the patient's body may need to be stimulated by the system. To facilitate this, additional electrodes 24 and/or distributors 26 could be connected to unused channels 32 of the existing distributors 26 of the system 10. Thus, expansion of the system 10 can be effected by implantation at the locality of the site of the patient's body rather than over an extensive part of the patient's body thereby again reducing the invasiveness of the procedure.

A further advantage of the present invention is that the total number of electrodes able to be utilised by the system is not limited to the fixed number of output channels of the stimulator unit 12. Rather the overall number of possible electrodes is increased through the use of distributors 26.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A multi-purpose, functional electrical stimulation (FES) system which includes:
    an implantable stimulator unit for stimulating a plurality of different sites in a patient's body;
    a transmitter adapted to be arranged externally of the patient's body for supplying signals transcutaneously to the stimulator unit;
    a controller in communication with the transmitter; and
    at least one implantable switching node having an input terminal in electrical communication with the stimulator unit and a plurality of output terminals to each of which one of a further switching node and a stimulating element is connected, the switching node including an addresser for switching at least one output terminal into electrical connection with the input terminal of the switching node in response to a control signal received from the controller via the stimulator unit.

2. The system of claim 1 which has a site switching node associated with each site.

3. The system of claim 2 in which intermediate switching nodes are arranged intermediate the stimulator unit and the site switching nodes.

4. The system of claim 3 in which a single lead extends from the stimulator unit to each of one of the site switching nodes and the intermediate switching nodes.

5. The system of claim 3 in which a multiplicity of leads extends from each site switching node, each lead terminating in at least one of the stimulating elements.

6. The system of claim 3 in which the addresser includes a switch element having the output terminals.

7. The system of claim 6 in which the switch element includes a switch member that connects a selected output terminal to the input terminal of the switching node.

8. The system of claim 7 in which the addresser includes control logic for controlling operation of the switch element under control of the controller.

9. The system of claim 8 in which the control logic receives control commands via the control signal received from the controller via the stimulator unit.

10. The system of claim 9 in which the control signal is a composite control signal and includes switching data relating to an output terminal to be selected and stimulation data for the stimulating element connected to the selected output terminal.

11. The system of claim 10 in which, where an intermediate switching node is connected to the selected output terminal, the composite control signal includes switching data for the output terminal of each switching node which is to be selected.

12. The system of claim 7 in which one of the output terminals is a non-stimulation terminal and, in a rest condition the switch member is connected to the non-stimulation output terminal.

13. The system of claim 12 in which a further output terminal is a status terminal which, when the switch member is connected thereto enables the condition of the switching node to be determined.

14. The system of claim 1 in which each switching node includes a power supply for supplying power to the addresser, the power supply being chargeable by a power component of the control signal.

15. The system claim 1 in which each stimulating element serves as a sensing element for sensing activity at the site at which it is located.

* * * * *